US008048018B2

(12) United States Patent
Millet

(10) Patent No.: US 8,048,018 B2
(45) Date of Patent: Nov. 1, 2011

(54) METHOD OF STIMULATING THE BODY

(75) Inventor: Oswald Millet, Vienna (AT)

(73) Assignee: Power-Wrap International Trading GmbH, Vienna (AT)

( * ) Notice: Subject to any disclaimer, the term of this patent is extended or adjusted under 35 U.S.C. 154(b) by 83 days.

(21) Appl. No.: 12/401,256

(22) Filed: Mar. 10, 2009

(65) Prior Publication Data

US 2009/0177140 A1 Jul. 9, 2009

Related U.S. Application Data

(63) Continuation of application No. 11/388,454, filed on Mar. 24, 2006, now abandoned, which is a continuation-in-part of application No. PCT/CH2004/000576, filed on Sep. 14, 2004.

(30) Foreign Application Priority Data

Sep. 25, 2003 (EP) .................................... 03405697

(51) Int. Cl.
*A61B 17/20* (2006.01)

(52) U.S. Cl. ........................................................ 604/22

(58) Field of Classification Search .................... 428/51, 428/52; 602/75; 604/22
See application file for complete search history.

(56) References Cited

U.S. PATENT DOCUMENTS

| | | | |
|---|---|---|---|
| 1,305,439 | A | 6/1919 | Brennan |
| 3,765,407 | A | 10/1973 | Prince |
| 4,705,028 | A | 11/1987 | Melby |
| 4,829,987 | A | 5/1989 | Stewart |
| 4,887,594 | A | 12/1989 | Siegel |
| 6,080,127 | A | 6/2000 | Li et al. |
| 6,465,709 | B1 | 10/2002 | Sun et al. |
| 6,520,926 | B2 | 2/2003 | Hall |
| 6,701,185 | B2 | 3/2004 | Burnett et al. |
| 6,884,227 | B2 | 4/2005 | Krompasick |
| 6,923,773 | B2 | 8/2005 | Leivseth et al. |
| 6,976,939 | B2 | 12/2005 | Harker et al. |
| 7,001,355 | B2 | 2/2006 | Nunomura et al. |
| 2002/0015689 | A1 | 2/2002 | Munro et al. |
| 2002/0082542 | A1 | 6/2002 | Hall |
| 2002/0115960 | A1 | 8/2002 | Redding, Jr. |
| 2004/0024348 | A1 | 2/2004 | Redding, Jr. |
| 2005/0137514 | A1 | 6/2005 | Vito et al. |
| 2006/0211977 | A1 | 9/2006 | Millet |
| 2006/0258963 | A1 | 11/2006 | Kopanic, Jr. et al. |

FOREIGN PATENT DOCUMENTS

| | | | |
|---|---|---|---|
| DE | 20115485 | U1 | 5/2002 |
| GB | 979184 | A | 1/1965 |
| WO | 02053084 | A1 | 7/2002 |
| WO | 03028599 | A2 | 4/2003 |
| WO | 2005027818 | A1 | 3/2005 |

OTHER PUBLICATIONS

International Search Report dated Nov. 23, 2004.

*Primary Examiner* — Nicholas D Lucchesi
*Assistant Examiner* — Aarti B Berdichevsky
(74) *Attorney, Agent, or Firm* — Laurence A. Greenberg; Werner H. Stemer; Ralph E. Locher

(57) ABSTRACT

A method for driving moisturizing substances and/or cosmetic active ingredients into the skin of the human body has skin brought into contact with the substances and/or active ingredients and a compression element applied thereto. Then, the tissue is subsequently set into oscillation. The compression element may be formed by compression bandages or compression wraps. The tissue may be set into oscillation in that the person locates himself on a vibrating support, or that the muscles of the person are stimulated by way of electrostimulation.

16 Claims, 3 Drawing Sheets

METHOD OF STIMULATING THE BODY

CROSS-REFERENCE TO RELATED APPLICATION

This application is a continuation of application Ser. No. 11/388,454, filed Mar. 24, 2006, which was a continuation-in-part under 35 U.S.C. §120 of international application PCT/CH2004/000576, filed Sep. 14, 2004, which designated the United States; the application also claims the benefit, under 35 U.S.C. §119, of European patent application No. 03 405 697.8, filed Sep. 25, 2003; the earlier applications are herewith incorporated by reference in their entirety.

BACKGROUND OF THE INVENTION

Field of the Invention

The invention relates to a method and a device for driving moisturizing and/or cosmetic active ingredients into the skin and to a method and a device for stimulating the body and of driving substances into the body.

It is known to apply creams, gels, lotions or oils which tauten and smooth the skin, onto the body. Cosmetic effects which are achieved with this may include a smoothing of the skin, a purifying of the tissue, and a combating of starbursts. It is likewise known to apply agents to the skin, using ointments, plasters, etc.

The disadvantage with this is the fact that the permeation of larger quantities of cosmetic creams, gels, lotions or oils or agents into the skin is a slow process, and the effect is accordingly slow and occurs in a weak manner. Furthermore, such products often contain for example strong irritants which are applied as an introduction agent for the active ingredients and achieve an intensive blood-circulation of the skin and the subcutaneous connective tissue. Strong irritants may however feel rather unpleasant.

It is the object of the invention to alleviate this.

SUMMARY OF THE INVENTION

It is accordingly an object of the invention to provide a method of stimulating the body which overcomes the above-mentioned disadvantages of the heretofore-known devices and methods of this general type.

With the foregoing and other objects in view there is provided, in accordance with the invention, a method of driving at least one of a moisturizing substance and cosmetically active ingredients into the skin of a human body, the method which comprises the following steps:

- bringing the skin into contact with the substance and/or the active ingredients;
- applying a compression element on the skin; and
- bringing a tissue connected to the skin into oscillation for driving the moisturizing substance and/or the cosmetically active ingredients into the skin.

The invention introduces the concept of actively introducing, thus driving in the moisturizing substances and/or cosmetic active ingredients rather than letting them passively permeate.

The invention therefore provides a method for driving in moisturizing substances and/or cosmetic active ingredients, which overcomes the disadvantages of existing procedures, and which in particular acts in an efficient manner on large surfaces.

This is effected in that the moisturizing substances and/or cosmetic active ingredients are driven into the skin of a human body, in that the skin which is in contact with these substances is applied onto a compression element, wherein the compression element may bear such that an oscillating-out (in the context of outward oscillation) of the tissue is prevented.

The oscillation is reflected back into the tissue on account of the compression element. The tissue is pressed against the compression element at least with the cycle of the excitation frequency, by which means substances to be introduced are driven in (almost "knocked in").

The term "cosmetic active ingredient" is to be understood here in a broad context. In particular, it includes every substance which cosmetically effectively influences or which tautens the skin, purifying substances, but also moisturizing substances, etc.

A "compression element" is to be understood as an element which is commonly cover-like, thus flat, flexible, and at least partly enveloping, which may be applied tightly to tissue. The compression element often has a certain elasticity so that it may be stretched in a taut manner.

The invention, according to another aspect, also concerns method of stimulating a human body or of driving substances into a human body or of stimulating a human body and driving substances into it, the method comprising the steps of applying a compression element to a skin surface, of placing the human body on a support, and of setting said support into oscillation so that tissue compressed by the compression element is set into oscillation.

Substances to be driven into a human body (the skin thereof or any other web) may be cosmetic or moisturizing substances.

The invention, according to yet another aspect, also concerns a device for stimulating a human body or for driving substances into a human body or for stimulating a human body and driving substances into it, the device comprising at least one of at least one compression bandage and of at least one compression wrap as well as an oscillation excitation apparatus operable to set human tissue into oscillation.

The method has at least the following basic advantages:

- Due to the fact that oscillation is excited in the tissue, the effect may be over a large area without having to operate with a great technical effort. In particular, means for exciting the oscillation need not be present over a large surface area or even on the whole surface of the tissue. It is sufficient to let the compression element bear on large surfaces of the tissue. This may be accomplished by large-surface, taut, elastic or non-elastic bandages or wraps. These bandages or wraps may furthermore be directly impregnated or laden with moisturizing substances and/or active ingredients,
- Larger quantities may be worked into the skin on account of the active driving-in of the moisturizing substances and/or cosmetic active ingredients,
- It may be shown that the human body, when it is excited into oscillation at least in part regions, is automatically exercised. For example, when standing on a support oscillating in a three-dimensional manner, the body by reflex compensates movements of the support. The training effect which may be achieved with this is considerable. This is similarly the case with electro-stimulation. The method according to the invention thus almost without any additional effort, may be combined with a training method which of course one again reinforces the cosmetic effect (fat reduction and local muscle tautening).
- The idea according to the invention, without further ado, permits an adaptation to the consistency of the tissue into which the moisturizing substances and/or cosmetic active ingredients are to be driven in. It is known that very different oscillation may be excited, depending on the stress/loading of the tissue. For example, low frequency oscillation is possible with very flabby tissue (example: "flabby tummy"). The method according to the invention may thus be adapted to the respective person when required by way of adapting the excitation frequency.

The invention according to one embodiment makes use of the fact that a multitude of oscillations are activated with "random" oscillation excitations. The oscillations amongst other things are standing or progressive waves in the tissue of the body, and the progressive waves have different directions of wave propagation. Amongst the excited waves there are transverse waves formed along the surface, whose wavelength for example is shorter than a dimension of the surface area covered by the compression element. Such waves are hindered by the compression element and this compression element prevents deflections. At those locations at which a deflection would be effected with free oscillation, the tissue is pressed against the compression element and where appropriate is slightly compressed. This effects a driving of the substances to be introduced into the tissue.

The excitation of oscillation may be effected in that the person stands (or sits or lies) on a support which executes oscillation. It has been shown that the method acts particularly well if the support carries out oscillations in several directions. For example, one may use a product with which a plate oscillates in a three-dimensional manner. Oscillation with frequencies between 10 Hz and 150 Hz, for example between 20 Hz and 90 Hz, particularly between 30 Hz and 50 Hz have been ascertained to be favorable. A particular effect is achieved if the vibrations are not limited to a single regular oscillation, but run in several dimensions and possibly not in a strict periodical manner. The frequency as well as amplitude may be matched to requirements of a person, for example to the tautness of the tissue.

Methods for exciting vibrations in a support, for example a plate are known. They may for example be based on rotating eccentric distancers between the vibrating plate and a stationary base. The details of such methods are not described in detail here.

One may also electro-stimulate as supplement to this type of oscillation excitation. A muscle contraction activity is excited by way of electro-stimulation. Here too, one may select the frequency, such that the desired oscillation to be excited is excited in a particularly intensive—almost resonant—manner, and/or that a particular training effect may be achieved.

Finally there is yet the possibility of oscillation by way of a belt vibration apparatus. Such may be applied on or at least partly next to a compression compress or compression wrap.

Other features which are considered as characteristic for the invention are set forth in the appended claims.

Although the invention is illustrated and described herein as embodied in a method of introducing cosmetics into the skin and for stimulating the human body, it is nevertheless not intended to be limited to the details shown, since various modifications and structural changes may be made therein without departing from the spirit of the invention and within the scope and range of equivalents of the claims.

The construction of the invention, however, together with additional objects and advantages thereof will be best understood from the following description of the specific embodiment when read in connection with the accompanying drawings.

DESCRIPTION OF THE PREFERRED EMBODIMENTS

Figure 1:
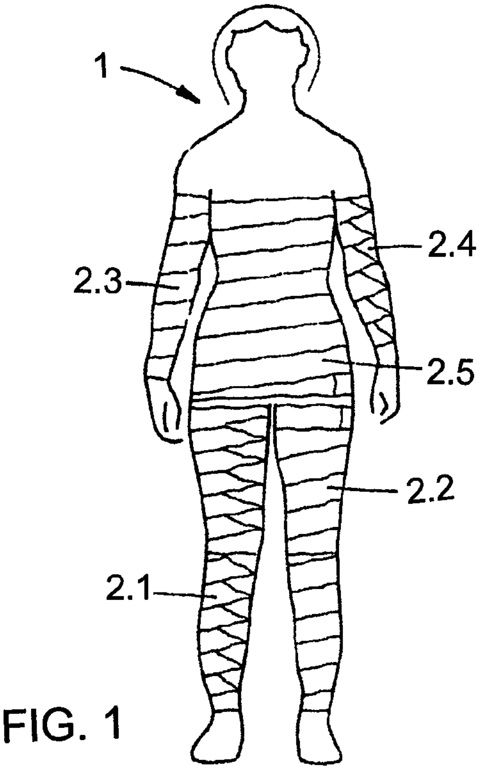
FIG. 1 is a front elevational view of a person with various types of compression compresses.

Referring now to the figures of the drawing in detail and first, particularly, to FIG. 1 thereof, there is seen a person with several compression elements 2.1, 2.2, 2.3, 2.4, 2.5 that bear on the body in a taut manner. These may be manufactured using elastic elements which are known per se, but which have a relatively large modulus of elasticity and therefore tighten in a taut manner, or using other materials which are at least slightly elastic. Moisturizing and/or cosmetically effective substances, possibly in a suitable solvent, are deposited below the compression compresses. As an alternative or to supplement this, the material of the bandages may also be impregnated with substances of this type. It is also possible to deposit several substances consecutively onto the skin.

Where appropriate (not illustrated), an outer covering which may for example be designed in a film-like manner is attached over the compress. This covering may likewise be tightened in a taut manner and further reinforce the effect of the compression bandage. Furthermore it may be essentially fluid-tight, and by way of this prevent pieces of clothing worn around the compress being soiled by substances with which the compress is impregnated or is soaked.

Figure 2:
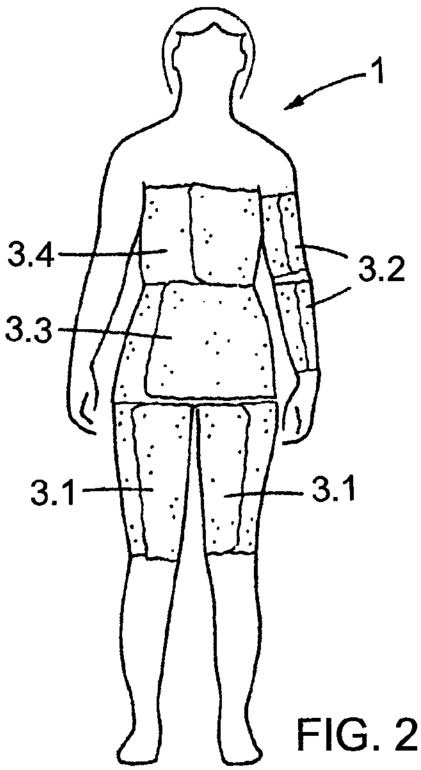
FIG. 2 is a similar view of a person with several compression wraps.

In FIG. 2, the person instead of compression bandages wears compression wraps 3.1, 3.2, 3.3, 3.4. These are likewise designed such that they may bear on the skin of a person in a taut manner. They may for example, similarly to blood pressure collars, comprise a reversibly actuatable closure, for example a so-called Velcro-type closure or something similar. Such a closure too, with at least slightly elastic wrap material and if some force is applied as is required, permits the wrap to bear snugly on the tissue. The wraps may also comprise additional means with which the snug bearing/pressure on the tissue are further improved or reinforced. Such additional means may contain self-inflating pressure bodies or ones to be inflated in the inside of the wrap etc.

Wraps which are sleeve like and may be closed are represented in the drawing. Closed and even stocking-like wraps are conceivable, which, where appropriate, may be slipped over with a suitable aid, similar to support stockings. The bandages may have an external essentially fluid-tight and hard-wearing layer, which renders any separate external covering superfluous. They may however be supplemented by a separate outer sleeve similar to the compress.

If it is not required, a piece of clothing may be worn over the compresses/wraps and in both cases one may do away with the covering/the outer layer.

Figure 3:
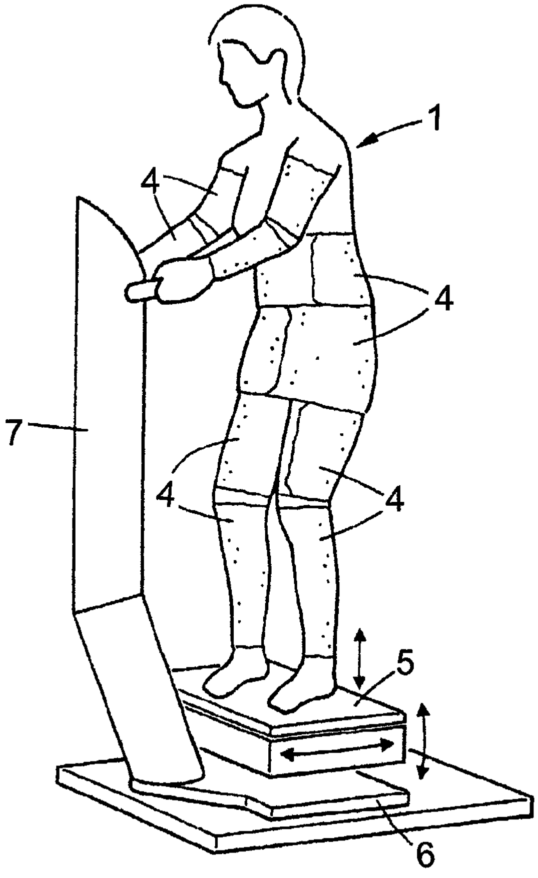
FIG. 3 is a perspective view of a person on a vibrating support.

In FIG. 3, the person 1 provided with compresses 4 stands on a three-dimensionally vibrating support, specifically a plate 5. The plate is attached on a stationary base 6. Drive means by way of which the plate is set onto oscillation in various directions of excursion are located between the plate 5 and the base 6. Oscillation in the body of the person are excited by way of vibrations of the pate 5. The persons holds tight on an optional support column 7, so that he does not have to concentrate on keeping his balance.

The multitude of oscillations which is excited in an inhomogeneous tissue which seen mathematically has an irregular shape, may not be described in a simple manner. Generally however an oscillation condition may be approximated by a linear (that is a mathematically independent) superimposition of natural oscillations. It may therefore be illustrative to consider individual oscillations from the simultaneously excited multitude of oscillations by themselves. For illustration, oscillations are represented in the figure which correspond to transverse waves running along the surface of the tissue. For such waves, it is the case that the propagation speed and thus with a given excitation frequency also the distance between two "wave peaks" is proportional to the root of the stress of the tissue (as a force). This means that the more flabby the tissue, the slower do the waves propagate and thus the farther apart are the "wave peaks."

Figure 4:
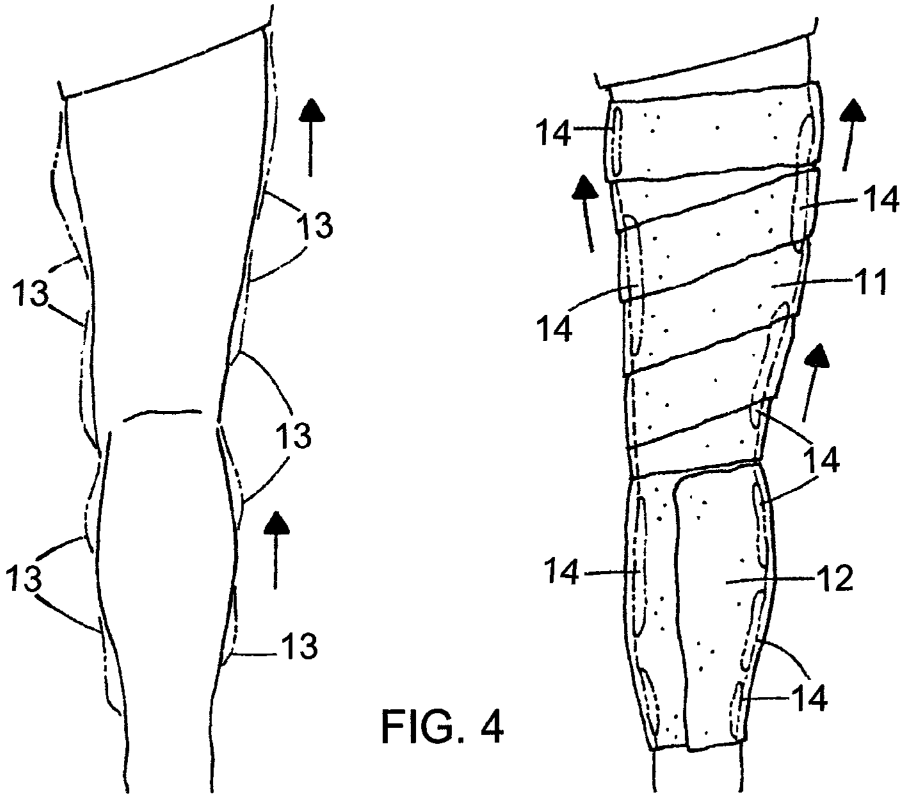
FIG. 4 illustrates the principle of the prevention of excursionary (outwardly moving) oscillation.

The effect of the compression element with oscillatory excitation is shown very schematically in FIG. 4. Both drawings of the figure for illustration show the leg of a person standing on a vibrating support. In the right-hand drawing, the person in each case wears a compress 11 preventing oscillations, and a sleeve 12 while the tissue may feely oscillate out in the left-hand drawing. The free, deflecting (outwardly-moving) oscillation is represented by wave amplitudes 13 advancing in the arrow direction.

In the right drawing, the tissue may not oscillate in a deflecting manner on account of the compression element formed by the compression bandage or the compression wrap. If such a compression wrap bears on the tissue, this acts on such oscillations as follows: An oscillation of the tissue with deflection (here also called "oscillating out") is prevented. Instead, the tissue, roughly at those locations where excursion would be present if no compression element were present, is pressed locally against the compression element and at the same time pressed together, and slightly compressed depending on the compressibility. The effect of this is to drive in the substances to be introduced, into the skin. Compressed locations 14 in the tissue are shown schematically in the figure.

Of course, compression elements have an influence on the design and propagation properties of the excited oscillations. This condition is not dealt with for simplifying the discussion serving merely for illustration by way of FIG. 4.

It is not necessary for oscillations to be present which entail propagating deflections in the case that no compression element is present. "Standing waves" may just as easily be formed, similar to the oscillations which result with a cable which is clamped at both sides. As mentioned, the actual condition of oscillation may be seen in any case as a superposition of a multitude of possible oscillation conditions.

Figure 5:
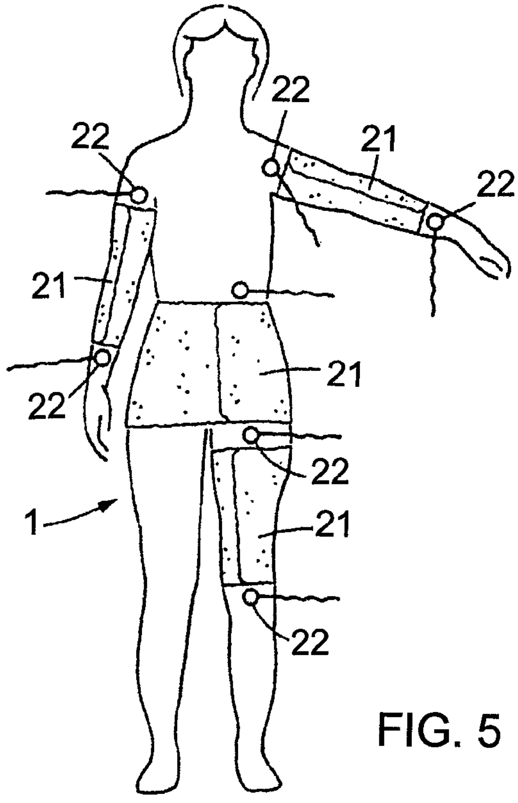
FIG. 5 is a front elevational view of a person with several compression compresses or wraps and with means for electro-stimulation.

In FIG. 5 a person is represented who wears compression compresses (bandages) 21 which are shown very schematically, as well as likewise very schematically drawn electrodes 22 of an electro-stimulation apparatus. The electro-stimulation apparatus is used in addition to the plate according to FIG. 3 which is capable of vibration, and likewise serves for exciting oscillation in the tissue. The excitation of muscle contractions via electro-stimulation is known per se and will not be explained in detail here.

Instead of the plate capable of vibration and the electro-stimulation apparatus, yet other further means for exciting oscillation in a tissue is conceivable. What is important within the context of the invention is that the tissue itself is excited into oscillation, and specifically generally such that it oscillates on the whole surface of the compression compress or wraps and not only in a pointwise manner. An alternative to a vibrating platform to be especially mentioned is a vibratory massage device.

An apparatus for driving in moisturizing substances into the skin comprises the following constituents:

a means for exciting oscillation in a human tissue, for example a plate capable of vibration, or an electro-stimulation apparatus;

at least one compression bandage and/or wrap. A plate capable of compression may be provided with an outer, substantially fluid-tight covering;

preferably moisturizing and/or cosmetically effective substances. These are either directly present in the bandage/wraps (i.e. the latter are at least partly impregnated with them) or they are provided in separate receptacles possibly additional cover material, essentially fluid-tight, for example a film.

The moisturizing and/or cosmetically effective substances may be present as gels, emulsions, creams, oils, lotions, etc. and have a broad combination of contained substances. Possible tissue- and skin-caring contents are known from cosmetics. They may contain water, oils and/or alcohols and at least some of the group of extracts from ginkgo leaves, ginseng roots, macadamia, Malva sylvestris, mint, balm, marigold, algae, olives, avocado, horse chestnut, bladderwrack, stinging nettle, horsetail, jojoba oil, maize oil, almond oil, wheat germ oil, and further natural ingredients as well as synthetic active ingredients.

Apart from cosmetically effective substances, also other substances may be applied by the method according to the invention such as any agent. Further, the method may also be used to stimulate the body without application of any product (without any active ingredient). In this way, it may enhance the blood circulation and stimulate Lymph flow.

An especially preferred embodiment of a device according to the invention includes a compression element which comprises a stimulating element with a plurality of inwardly facing neps. The stimulating element (or "nepped element") may have any shape with neps facing towards the skin. It may be formed as a collar or sleeve or may simply be a laminar element with a plurality of protruding neps. As yet another alternative, the stimulating element may be formed as a soft, elastically deformable laminar element with a plurality of hard knots serving as neps if pressure is applied between the laminar element and skin adjacent thereto.

Figure 6:
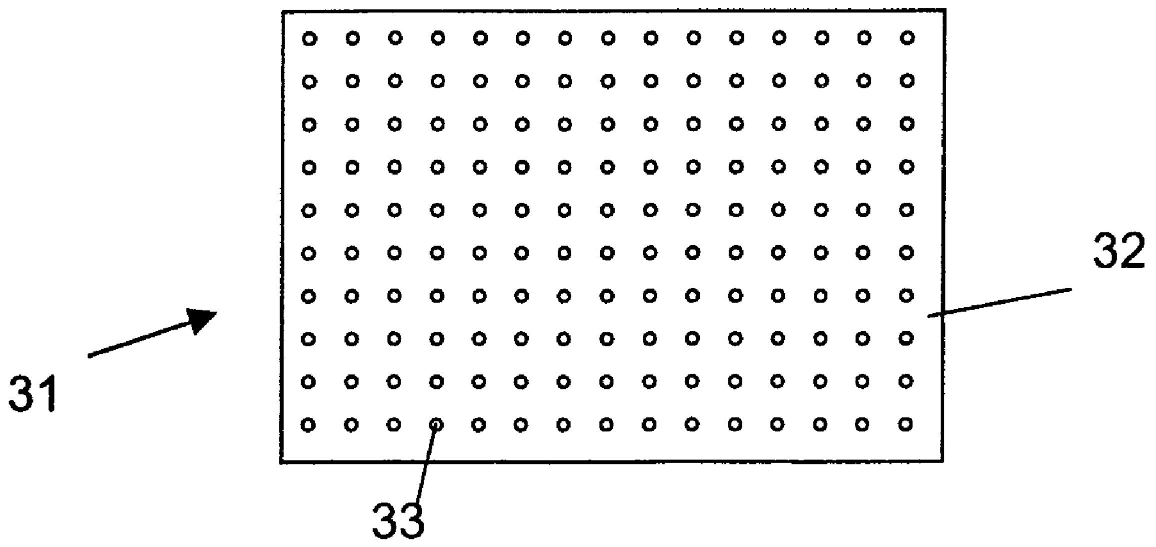
FIG. 6 is a plan view of a nepped element.

An example of a stimulating element 31 is shown in FIG. 6. The stimulating element is a silicone film 32 with a plurality of silicone neps 33 protruding on one side.

The stimulating element is preferably at least partially made from silicone, for example, at least the neps are made from silicone. The stimulating element may be used in combination with a wrap or a sleeve. For example, a stimulating element may be placed on top of a wrap or sleeve of the above-described kind. The stimulating element—if it is not formed as closed collar—may then be surrounded by an elastic foil keeping it in place. Additionally or as an alternative, the stimulating element may be formed as trousers, a sleeve, or a wrap or bandage with inwardly facing neps.

I claim:

1. A method of driving at least one of a moisturizing substance and cosmetically active ingredients into the skin of a human body, the method which comprises:

bringing the skin into contact with the substance and/or the active ingredients;

applying a compression element on the skin;

positioning the human body on an oscillating support; and causing the oscillating support to oscillate at a frequency of between 10 Hz and 150 Hz to thereby bring a tissue connected to the skin into oscillation for driving the moisturizing substance and/or the cosmetically active ingredients into the skin.

2. The method according to claim 1, which comprises applying the compression element to substantially prevent a deflecting oscillation of the tissue.

3. The method according to claim 1, wherein the applying step comprises placing a compression element in the form of a tautly tensioned elastic bandage or wrap.

4. The method according to claim 3, which comprises attaching a film around the elastic bandage or wrap.

5. The method according to claim 1, which comprises additionally triggering contraction activity of muscles by electro-stimulation.

6. The method according to claim 1, which comprises locating the human body on the oscillating support at a location of the body that is different from a location bearing the compression element.

7. A device for stimulating a human body and/or for driving substances into a human body or for stimulating a human body and driving substances into the body, the device comprising: at least one compression device selected from the group consisting of a compression bandage and a compression wrap configured to be placed on the body, and an oscillation excitation apparatus operable to oscillate with a frequency of between 10 Hz and 150 Hz and to set human tissue into oscillation.

8. The device according to claim 7, wherein said oscillation excitation apparatus comprises a support with an electrically operable drive configured to excite said support into oscillation, wherein said support is configured to support a human body standing thereon and wherein said drive is configured to set said support into oscillation when the human body stands on said support.

9. The device according to claim 8, which further comprises an electro-stimulation apparatus for stimulating contraction activity of muscles.

10. A method of stimulating a human body and/or of driving substances into a human body, the method which comprises the steps of applying a compression element to a skin surface, placing the human body on a support, and setting the support into oscillation at a frequency of between 10 Hz and 150 Hz to cause tissue compressed by the compression element into oscillation.

11. The method according to claim 10, wherein the compression element is a compression bandage or a compression wrap.

12. The method according to claim 10, which comprises, prior to applying the compression element to the skin surface, applying at least one of a cosmetic substance, an agent, and an active ingredient to the skin surface and/or to the compression element.

13. The method according to claim 10, wherein the compression element comprises a nepped element formed with neps facing towards the skin.

14. The method according to claim 13, wherein the nepped element is at least partially made of silicone.

15. The method according to claim 13, wherein the compression element further comprises a wrap or a sleeve underneath the nepped element.

16. The method according to claim 13, which comprises surrounding the nepped element by an elastic foil.

* * * * *